US009023049B2

(12) United States Patent
Berberich et al.

(10) Patent No.: US 9,023,049 B2
(45) Date of Patent: May 5, 2015

(54) MEDICAL PUNCTURING DEVICE

(75) Inventors: Sascha Berberich, Tuttlingen (DE); Sebastian Frey, Waghaeusel (DE)

(73) Assignee: Karl Storz GmbH & Co. KG (DE)

( * ) Notice: Subject to any disclaimer, the term of this patent is extended or adjusted under 35 U.S.C. 154(b) by 355 days.

(21) Appl. No.: 13/414,421

(22) Filed: Mar. 7, 2012

(65) Prior Publication Data

US 2012/0232558 A1 Sep. 13, 2012

(30) Foreign Application Priority Data

Mar. 7, 2011 (DE) ......................... 10 2011 013 888

(51) Int. Cl.
*A61B 17/16* (2006.01)
*A61B 17/29* (2006.01)

(52) U.S. Cl.
CPC ......... *A61B 17/1604* (2013.01); *A61B 17/1631* (2013.01); *A61B 17/1675* (2013.01); *A61B 2017/2927* (2013.01)

(58) Field of Classification Search
CPC ............................ A61B 17/16; A61B 17/1604
USPC ........... 606/79, 84, 86 R, 167, 170, 184–186; 30/167, 167.1, 358, 363
See application file for complete search history.

(56) References Cited

U.S. PATENT DOCUMENTS 3,990,453 A * 11/1976 Douvas et al. ................ 606/107
4,122,855 A * 10/1978 Tezel ............................ 606/131
5,431,671 A * 7/1995 Nallakrishnan ............... 606/167
5,836,958 A * 11/1998 Ralph ........................... 606/160
5,871,204 A * 2/1999 Spirer ......................... 254/26 R
5,922,000 A * 7/1999 Chodorow .................... 606/167
5,928,239 A * 7/1999 Mirza ............................ 606/79
5,957,925 A * 9/1999 Cook et al. ...................... 606/87
6,830,574 B2 * 12/2004 Heckele et al. ............... 606/104
7,749,228 B2 * 7/2010 Lieberman ...................... 606/84
8,251,915 B2 * 8/2012 Dunn ........................... 600/564
8,267,958 B2 * 9/2012 Braun ........................... 606/205
8,551,098 B2 * 10/2013 Shimko et al. .................. 606/84
8,622,925 B2 * 1/2014 Dunn ........................... 600/564
8,641,718 B2 * 2/2014 Meridew ..................... 606/86 R
2001/0021853 A1 9/2001 Heckele et al.
2004/0059338 A1 3/2004 Ebner
2005/0113838 A1 * 5/2005 Phillips et al. .................. 606/80
2005/0273111 A1 * 12/2005 Ferree et al. .................... 606/84
2006/0074427 A1 * 4/2006 Lieberman ...................... 606/84
2006/0074428 A1 4/2006 Ralph et al.
2006/0198877 A1 9/2006 Steinwachs et al.
2006/0235419 A1 * 10/2006 Steinwachs et al. ............ 606/86

(Continued)

FOREIGN PATENT DOCUMENTS

DE 102005010988 A1 9/2006
DE 102005010989 A1 9/2006

(Continued)

*Primary Examiner* — Christian Sevilla
*Assistant Examiner* — Eric S Gibson
(74) *Attorney, Agent, or Firm* — St. Onge Steward Johnston & Reens LLC

(57) ABSTRACT

A medical puncturing serves for penetrating into a bone or a cartilage. It has a shaft and a tool carrier connected with its proximal end to a distal end of the shaft. The tool carrier has a puncturing tool being a punch or a multi-fracture chisel. The tool carrier is connected at its proximal end via a freely articulated joint to the distal end of said shaft. A stop limits a laterally pivoting movement of said tool carrier to a maximum angle of 45°.

9 Claims, 5 Drawing Sheets

(56) References Cited

U.S. PATENT DOCUMENTS

| | | | | |
|---|---|---|---|---|
| 2010/0076440 | A1 | 3/2010 | Pamichev et al. | |
| 2012/0232558 | A1* | 9/2012 | Berberich et al. | 606/84 |
| 2012/0271313 | A1* | 10/2012 | Lauchner | 606/84 |

FOREIGN PATENT DOCUMENTS

| | | | |
|---|---|---|---|
| DE | 102005014624 | A1 | 10/2006 |
| DE | 102009001278 | A1 | 9/2010 |
| WO | 2011014677 | A1 | 2/2011 |

* cited by examiner

MEDICAL PUNCTURING DEVICE

BACKGROUND OF THE INVENTION

The invention relates to a medical puncturing device for penetration into a bone or a cartilage.

A medical puncturing device in the form of a cartilage punch is known, for example, from DE 10 2005 010 988 A1.

With such a punch, an area of the cartilage-like periosteum can be punched out from a bone surface. This is done if the periosteum has a defect, for example, and if this defect site has to be repaired, for example by fitting a suitable implant.

Defect sites of this kind occur particularly in joints where two opposite bones rub against each other. In healthy joints, a corresponding layer of cartilage is located between the bones, and also a cartilage fluid that lubricates the movement of the two bones on each other.

If this synovial fluid is no longer present, either because of injuries or sometimes also because of aging, the bones rub directly on each other via their cartilage or via the outer periosteum thereof. Very painful defects then arise at the contact sites.

To rectify the defect, a flat piece of the periosteum is first of all punched out in the area of the defect using a puncturing device in the form of a punch that has a distal cutter. The shaft of the puncturing device is hollow, such that the punched-out piece of periosteum can be removed through the shaft. For the subsequent successful fusion of an implant, it is very important that the cut provided by the circumferential cutter is made with a cut edge that is as straight as possible, particularly with a cut edge that extends perpendicularly with respect to the surface described by the cutter.

A medical puncturing device in the form of a microfracture chisel is known from DE 10 2005 010 989 A1.

This puncturing device has a plurality of studs or tips projecting from the distal end. These are designed to introduce microfractures into a bone. By means of these microfractures, a clot permeated with pluripotent stem cells from the bone marrow can be generated. Such a clot is also sometimes known as a "super clot". The stem cells contained in this clot can differentiate to cartilage cells in the course of the healing process and form new cartilage tissue. That is to say, this microfracture chisel can likewise be used in the repair of cartilage defects on bone.

For example, after the periosteum in the area of the defect site has been removed using the punch mentioned in the introduction, a multi-microfracture chisel can be used to create such a clot, which then replaces the cartilage at the punched-out site.

It has also been found that the fusion of an implant fitted at the punched-out site is greatly accelerated by such clots.

A common aspect of both tools is that, during handling, a force has to be applied along the longitudinal axis of the shaft, either to press the cutter of the punch into the cartilaginous tissue or to drive the multi-microfracture chisel into the bone.

The fact is, however, that such defect sites mostly occur quite far inwards in the area of joints, particularly in the area of the knee joint, that is to say at a location that is quite difficult to access using a rectilinearly extending and rigid shaft. The joint then has to be bent or spread to an extreme in order to access such locations.

Therefore, the object of the present invention is to remedy this situation and to improve a puncturing device of the type mentioned at the outset in such a way that it is also possible to reach locations that are quite difficult to reach in joints, in order to repair a defect site there.

SUMMARY OF THE INVENTION

According to the invention, the object is achieved by a puncturing device for penetrating into a bone or a cartilage, comprising a shaft having a longitudinal axis, a tool carrier having a distal end and a proximal end, said tool carrier having a longitudinal axis, a puncturing tool arranged at said distal end of said tool carrier, said puncturing tool being a punch or a multi-fracture chisel, said tool carrier being connected at its proximal end via a freely articulated joint to a distal end of said shaft, said tool carrier can pivot about said joint from an orientation having said axis of said shaft and said axis of said tool carrier coaxial and an orientation having said axis of said tool carrier pivoted laterally, with said axis of said tool carrier standing under an angle to said axis of said shaft, and a stop limiting said laterally pivoting movement of said tool carrier to an maximum angle of 45°.

By means of the pivotability of the tool carrier, the puncturing device can be brought towards the target with the shaft arranged obliquely or tilted with respect to the bone surface that is to be treated. By means of the freely pivotable tool carrier, the tool carrier can easily be oriented such that the distal end face thereof comes to lie with the tool approximately parallel to the surface that is to be punctured.

The expression "freely pivotable" means that the pivotability can be achieved without the aid of other auxiliary means or control means, like push rods, wires etc.

In this way, the actual tool, that is to say either the punch with the circumferential cutter or the multi-microfracture chisel with the distally projecting pins, can be driven into the periosteum in an orientation that ensures an optimal result. As has been mentioned, an optimal result is achieved, in the case of punching, when the cutter of the punch, which is in most cases circular in circumference, is pressed inwards in an orientation in which the plane delimited by the punch lies parallel to the bone surface. The cutting edge of the punch lies in a plane perpendicular to the longitudinal axis of the tool carrier. The pins of the chisel project in a direction of the longitudinal axis of the tool carrier.

On the circumferential cartilage wall that remains, this then generates a defined edge of the remaining periosteal tissue, which edge rises approximately at right angles from the bone surface. The same applies to the multi-microfracture chisel. Here too, an optimal result is achieved when the pins of the chisel are driven in a direction perpendicular to the bone surface.

By means of the pivotability of the tool carrier, it is now possible to treat the relatively inaccessible locations and, in doing so, to orient the actual tool with respect to the bone surface as if it were a non-pivotable, rigid rectilinear shaft.

By the provision of a stop that limits the pivoting movement to a maximum of 45°, it is possible, to exert strong forces in the direction of the longitudinal axis of the shaft, which are transmitted via the pivoted tool carrier in a direction perpendicular to the bone surface. This can be done up to angles of 45° without a great risk of tilting the tool carrier from the bone surface.

The stop can be provided at the distal end of the shaft or at the proximal end of the tool carrier or at both parts.

In other words, the force needed to penetrate the tool, that is to say either to press it in or drive it in, can still be exerted in the usual manner by the operator, since the fact that the angle is limited to a maximum of 45° ensures that a sufficiently large part of this force is exerted in the desired direction perpendicular to the bone surface.

By means of the embodiment according to the invention, a considerably wider range of application of this repair technique is achieved, since such defects can now be repaired on bone surfaces lying much farther inwards, without the two bones having to be moved towards each other or drawn away from each other to an extreme.

Finally, a procedure of this kind can also be carried out in a manner that causes the patient much less trauma.

In one embodiment of the invention, the pivoting angle is limited to a maximum of 30°.

This measure has the advantage that, because of this limitation of the angle, a large part of the forces exerted in the direction of the longitudinal axis of the shaft can be conveyed via the actual tool perpendicular to the bone surface during puncturing. This embodiment is particularly advantageous if cartilage defects are to be carried out on parts lying relatively far outside in a joint, particularly in the peripheral area of the knee joint.

In another embodiment of the invention, the pivoting angle is limited to a maximum of 15° by the stop.

This embodiment has the advantage that virtually the entire driving-in force can be transferred to the tool.

This embodiment will be used when areas of a joint that lie far outside are to be worked with the puncturing device and it is necessary to transfer high forces. By virtue of the fact that most of the exerted force is conveyed through the tool into the bone, it is not necessary to apply such high forces as in the case of more strongly angled tool carriers, in which there is the tendency for the tool carrier to shift sideways or tilt under strong forces.

In another embodiment of the invention, the tool carrier has an axial length of at most 30 mm, in particular 20 mm, or most preferably only 10 mm.

These embodiments have the advantage that, because of the short axial length of the tool carrier, only a relatively small space is needed between two opposite bones in order to push the tool in between these bones and carry out the piercing procedure. In the knee joint, such clearances can be achieved by extreme angling of the lower leg relative to the upper leg, such that defects lying quite far inwards in the joint can already be worked on without additional spreading measures.

In another embodiment of the invention, the tool carrier is freely pivotable about an axle extending transversely with respect to the longitudinal axis of the shaft.

This measure not only has the advantage that the articulated and thus pivotable connection between shaft and tool carrier can be provided by mechanically very simple means, but also that the axle constitutes a mechanically stable means of ensuring that the forces acting on the shaft can be transferred to the tool carrier.

This resulting pivot axis, provided by the axle and extending transversely with respect to the longitudinal axis, also gives the operator a clear indication of which direction the tool carrier can pivot in. It gives him an orientation aid as to how he has to insert the medical puncturing device between the two bones, for example in a knee joint, in order to achieve the desired orientation either of the punch or of the multimicrofracture chisel.

In another embodiment of the invention, the tool carrier is mounted on the shaft via a ball-and-socket joint so as to be freely pivotable in all directions.

This measure has the considerable advantage that the tool carrier is freely pivotable in all directions from the longitudinal axis. The tool carrier can pivot about the ball-and-socket joint solely by gravity when held at a tilt.

In another embodiment of the invention, the stop has an oblique stop surface on the distal end of the shaft.

This measure has the advantage that, by mechanically simple and robust means, a stop surface is formed that arrests the pivoting movement of the tool carrier. By suitable design of the stop, the maximum pivoting angle can then be limited in one and the same tool carrier with correspondingly different shafts, for example to the aforementioned values of under 45°, for example at most 30° or at most 15°.

At the maximum pivoting angle, the stop surface provides relatively large contact surface between tool carrier and shaft, via which contact surface the necessary forces can be transferred during puncturing.

In another embodiment of the invention, the stop surface is designed in such a way that a pivoting movement from the longitudinal axis can be performed only to one side.

This measure has the advantage that the tool carrier is pivotable from the longitudinal axis quite specifically about a pivot axis and only in a single direction. Some surgeons want to have only one possible direction of pivoting.

This can be achieved, for example, by the fact that the distal end face of the shaft is bevelled only on one side, such that the tool carrier is permitted a pivoting movement only in the direction of this bevel. The angle of this bevel permits the adjustment of the different maximum pivoting angles. Of course, the stop as such also comprises a stop surface on the proximal end of the tool carrier, which stop surface, during pivoting of the tool carrier, then comes into contact with the corresponding stop surface on the distal end of the shaft, and the pivoting movement is thus limited.

In another embodiment of the invention, the tool carrier is connected to a hollow cylindrical shaft via a kind of hinge joint, and the body of the tool carrier is likewise designed as a hollow cylinder, wherein the socket and joint head of the hinge joint are shaped from the hollow cylindrical wall of the shaft and the hollow cylindrical tool carrier, respectively.

This measure has the advantage that almost the entire interior of the hollow cylindrical shaft and of the hollow cylindrical tool carrier is available for manipulations. This embodiment is particularly advantageous in the embodiment as a punch, since the piece of cartilage punched out by the punch is intended to be carried through this hollow interior by a spatula and removed. The socket and joint head of the hinge joint are shaped from the walls. The joint head can protrude proximally from the tool carrier or distally from the distal end of the hollow cylindrical shaft. Correspondingly, the socket is then cut out in the opposite cylinder wall of the corresponding component. In modern technology, this can be done with great precision by laser cutting or the like, and the parts are easy to join together. The pivotability is then achieved by suitable bevelling, for example of the distal front edge of the wall of the shaft or of the correspondingly opposite face of the tool carrier or by both, such that variable pivoting angles and also pivoting directions can then be provided.

It will be appreciated that the aforementioned features and the features still to be explained below can be used not only in the respectively cited combination but also in other combinations, without departing from the present invention.

BRIEF DESCRIPTION OF THE DRAWINGS

The invention is described and explained below on the basis of a number of selected illustrative embodiments and with reference to the attached drawings, in which:

FIG. 10 shows the end position of the puncturing device, with the punch correctly aligned before starting to be pressed in.

DESCRIPTION OF PREFERRED EMBODIMENTS

Figure 1:
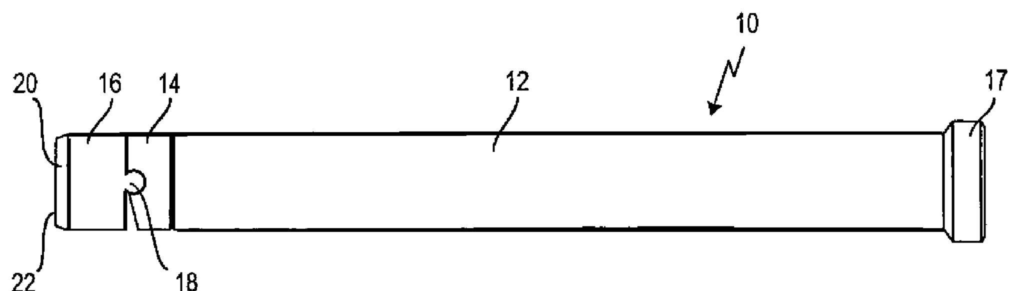
FIG. 1 shows a side view of a first illustrative embodiment of a puncturing device in the form of a punch, FIG. 2. shows, in a perspective view, a longitudinal section through the device from FIG. 1.
Figure 2:
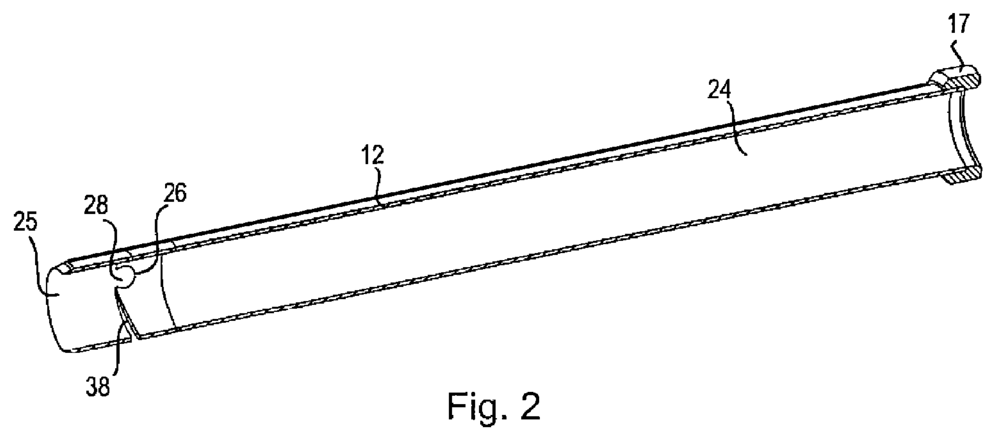
Figure 3:
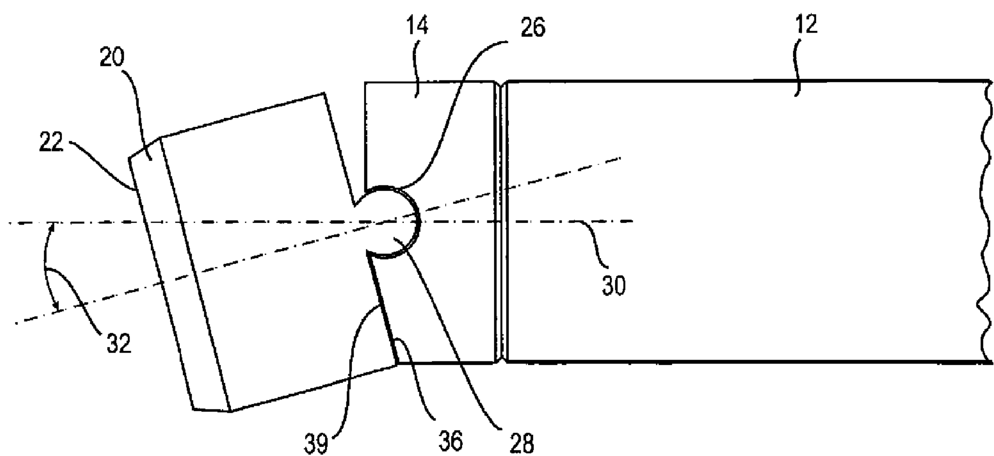
FIG. 3 shows a greatly enlarged side view of the distal end area of the puncturing device with an angled tool carrier.

A first illustrative embodiment of a puncturing device according to the invention is shown in FIGS. 1 to 3 and is designated overall by reference number 10.

The puncturing device 10 has a shaft 12, on the distal end 14 of which a tool carrier 16 is mounted in an articulated manner and is thus pivotable. The proximal end of the shaft 12 is provided with a strike head 17 via which a force can be applied to the shaft 12, for example by a suitable driving-in tool, such as a hammer or the like.

The tool carrier 16 is connected to the shaft 12 via a joint 18.

The tool 20 at the distal end of the tool carrier 16 is designed as a circumferentially wedge-shaped punch with a cutter 22.

The shaft 12 is designed as a hollow cylinder 24 and the tool holder 16 as a hollow cylinder 25, as can be seen in particular from the cross-sectional view in FIG. 2.

The joint 18 is designed in the manner of a hinge joint. At diametrically opposite locations on the distal end 14 of the shaft 12, a socket 26 is cut out in the wall of the hollow cylinder 24.

Correspondingly shaped joint heads 28 protrude from the proximal end of the tool carrier 16, said joint heads 28 having likewise been worked out from the wall of the hollow cylinder 25. A joint head 28 fits into a socket 26. Suitable dimensioning avoids lateral sliding of the tool carrier 16 and shaft 12 away from each other transversely with respect to the longitudinal axis 30. In the orientation of FIGS. 1 and 2 a longitudinal center axis of shaft 12 runs coaxial with a longitudinal center axis of the tool carrier 16.

The tool carrier 16 can pivot about the joint head 28 away from the longitudinal axis 30 of the shaft 12, specifically through a pivoting angle 32 of at most 15° (see FIG. 3).

A stop 36 limits this pivoting movement, which is possible only in a single direction away from the longitudinal axis 30, specifically downwards in the view in FIG. 3.

The stop 36 consists of a bevelled stop surface 38 on the distal end 14 of the hollow cylindrical shaft 12. This inclined stop surface 38 thus represents an approximately semi-circular, bevelled front face of the distal end 14 of the shaft 12, which front face extends about half a circle between the opposite sockets 26.

The front face lying radially opposite this stop surface 38 extends approximately at right angles to the longitudinal axis 30.

The proximal front face or end face 39 of the hollow cylindrical tool carrier 16 is designed as a circumferential edge whose plane extends perpendicularly with respect to the longitudinal axis of the tool carrier 16.

The pivoting range of the tool carrier 16 thus lies between the rectilinear orientation shown in FIG. 1, that is to say in alignment with the longitudinal axis 30, and the position in which it is pivoted through 15° in one direction, as seen in FIG. 3.

Figure 4:
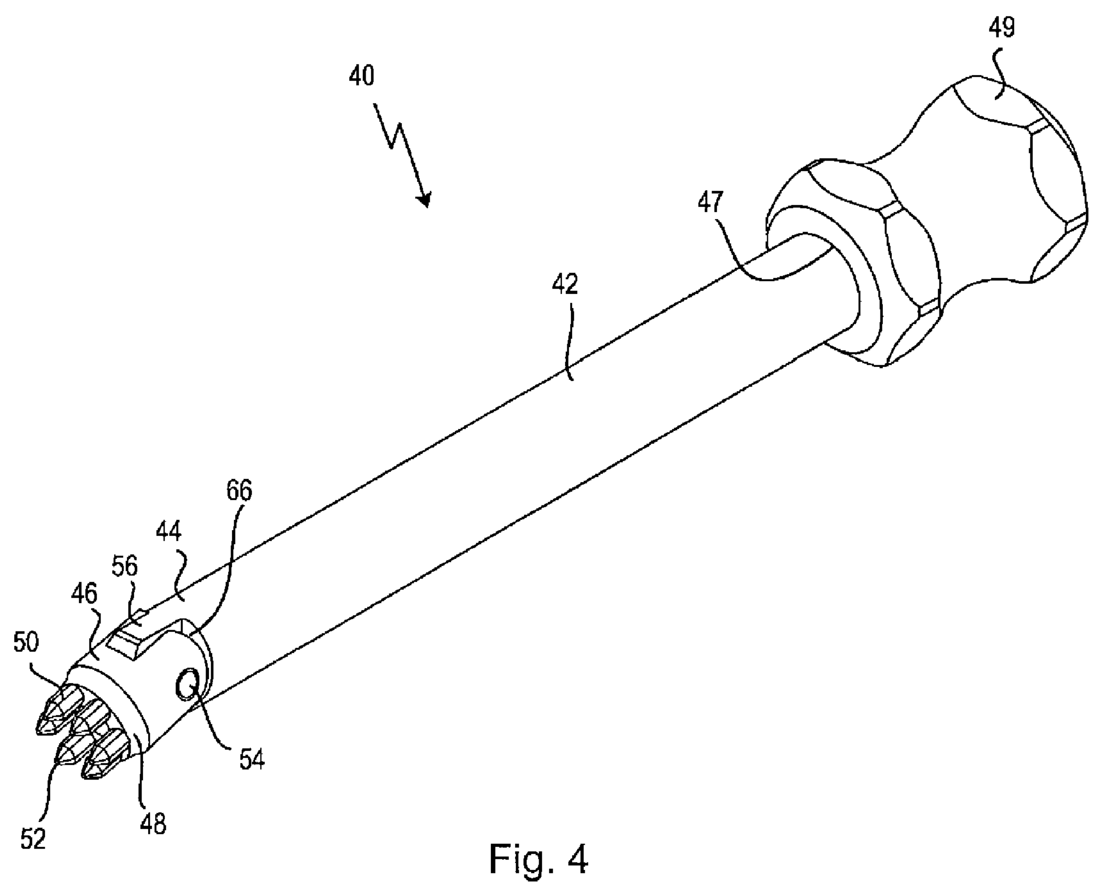
FIG. 4 shows a perspective view of a second illustrative embodiment in the form of a multi-microfracture chisel.
Figure 5:
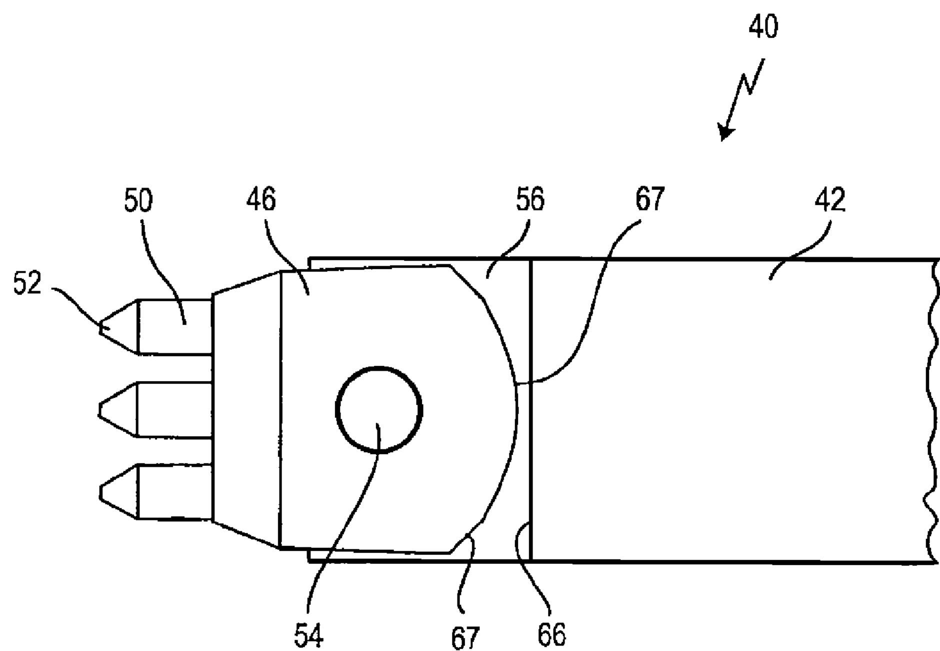
FIG. 5 shows a greatly enlarged side view of the distal end area of the puncturing device from FIG. 4, with the tool carrier oriented rectilinearly.
Figure 6:
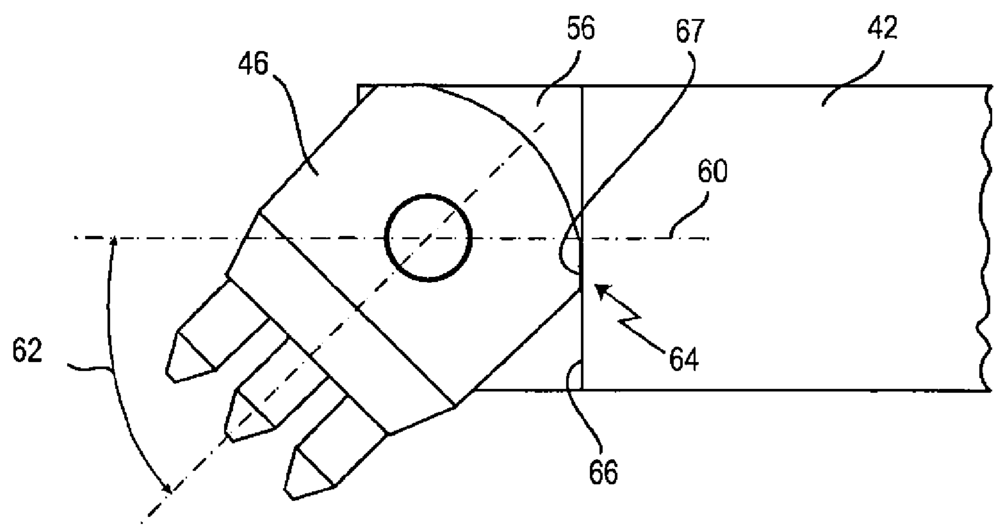
FIG. 6 shows a side view corresponding to FIG. 5, with the tool carrier angled to the maximum extent.

A second illustrative embodiment of a puncturing device according to the invention is shown in FIGS. 4 to 6 and is designated overall by reference sign 40.

The puncturing device 40 likewise has a rectilinearly extending, elongate shaft 42, at the distal end 44 of which a tool carrier 46 is mounted in an articulated manner.

The tool carrier 46 carries at its distal end a tool in the form of a multi-microfracture chisel 48. This chisel has a plurality of distally projecting studs 50, which each end in a tip 52. The proximal end of the shaft 12 is provided with a handle 49.

The articulated connection between shaft 42 and tool carrier 46 is provided via an axle 54, which runs transversely with respect to the longitudinal axis 60 of the shaft 42 and extends through a central web 56, which projects distally from the shaft 42, and through two proximally protruding fork arms (not shown in detail here) of the tool carrier 46. The stop 64 is formed by corresponding stop surfaces 66 on the distal end of the shaft 42, from which the web 56 protrudes. This stop surface 66 extends perpendicularly with respect to the longitudinal axis 60. The tool carrier 46 has a proximal end face that is curved approximately in an arc shape and that then abuts against this stop surface 66.

FIG. 6 shows a situation in which the tool carrier 46 is pivoted about the axle 54 through its maximum pivoting angle 62 of approximately 45°. In this position of maximum pivoting, the end face 67 of the tool carrier 46 strikes the stop surface 66 on the distal end of the shaft 42. The tool carrier 46 can also be pivoted in the opposite direction through the maximum pivoting angle 62 of approximately 45°.

Figure 7:
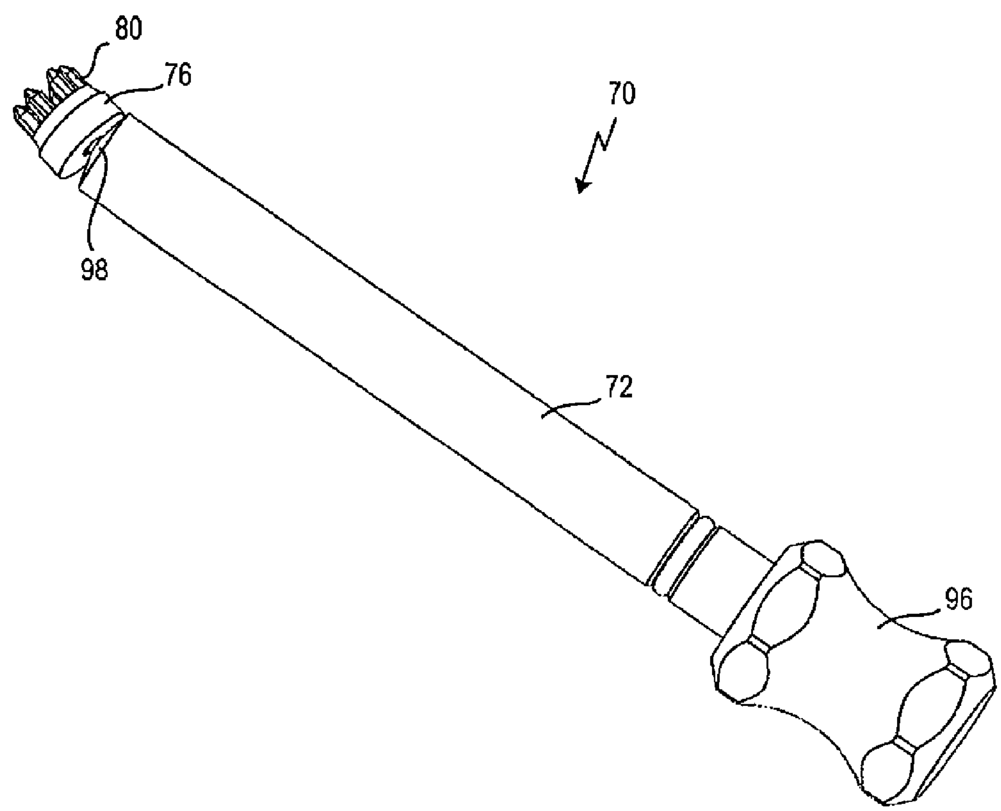
FIG. 7 shows a perspective view of a third illustrative embodiment of a puncturing device, in which the tool carrier is connected to the shaft via a ball-and-socket joint.
Figure 8:
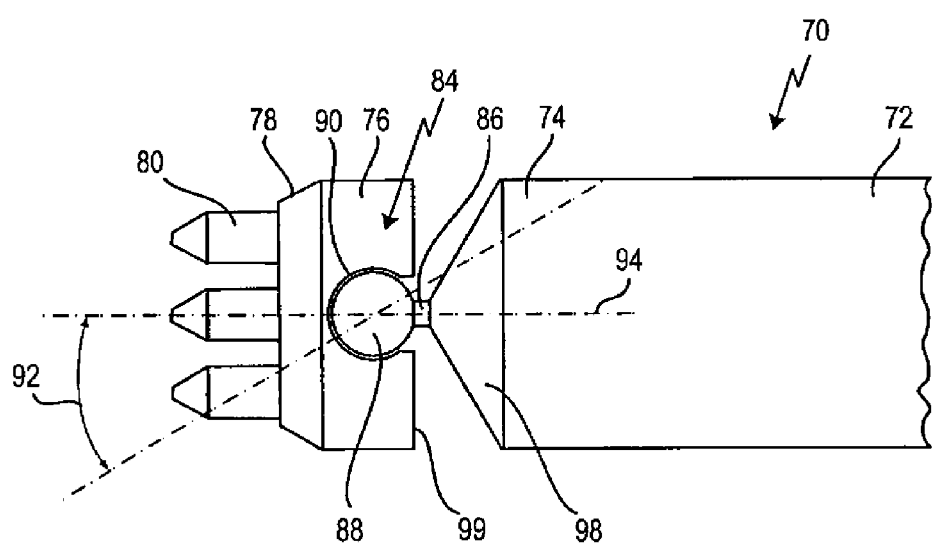
FIG. 8 shows a greatly enlarged side view of the distal end area of the puncturing device from FIG. 7.

A third illustrative embodiment of a puncturing device according to the invention is shown in FIGS. 7 and 8 and is designated overall by reference number 70.

The puncturing device 70 is designed similarly to the puncturing device 40 and has an elongate shaft 72 on the distal end of which a tool carrier 76 is mounted, whose actual tool is designed as a multi-microfracture chisel 78 with the correspondingly protruding studs 80. The articulated connection between shaft 72 and tool carrier 76 is effected here via a ball-and-socket joint 84, as can be seen in more detail in FIG. 8. The ball-and-socket joint 84 has a stud 86, which protrudes from the distal end 74 of the shaft 72 and which carries a ball 88. The ball 88 is received in a ball socket 90 in the interior of the tool carrier 76. The stop 98 is formed by a conically shaped, distally projecting end face 98 of the distal end of the shaft 72. This cone face cooperates with the proximal end face 99 of the tool carrier 76, which proximal end face 99 extends perpendicularly with respect to the longitudinal axis 94 of the puncturing device 70 in the orientation shown in FIG. 8.

The maximum pivoting angle 92 is in this case 30°, and the ball-and-socket joint 84 means that a pivoting movement out from the longitudinal axis 94 is possible laterally in all directions. The ball-and-socket joint 84 is designed such that the tool carrier 76 can move freely about the ball 88 without the use of any auxiliary means. The proximal end of the shaft 72 is provided with a handle 96. The two illustrative embodiments of puncturing devices 40 and 70 each serve as "multi-microfracture chisels", that is to say for making punctures in a bone surface.

Figure 9:
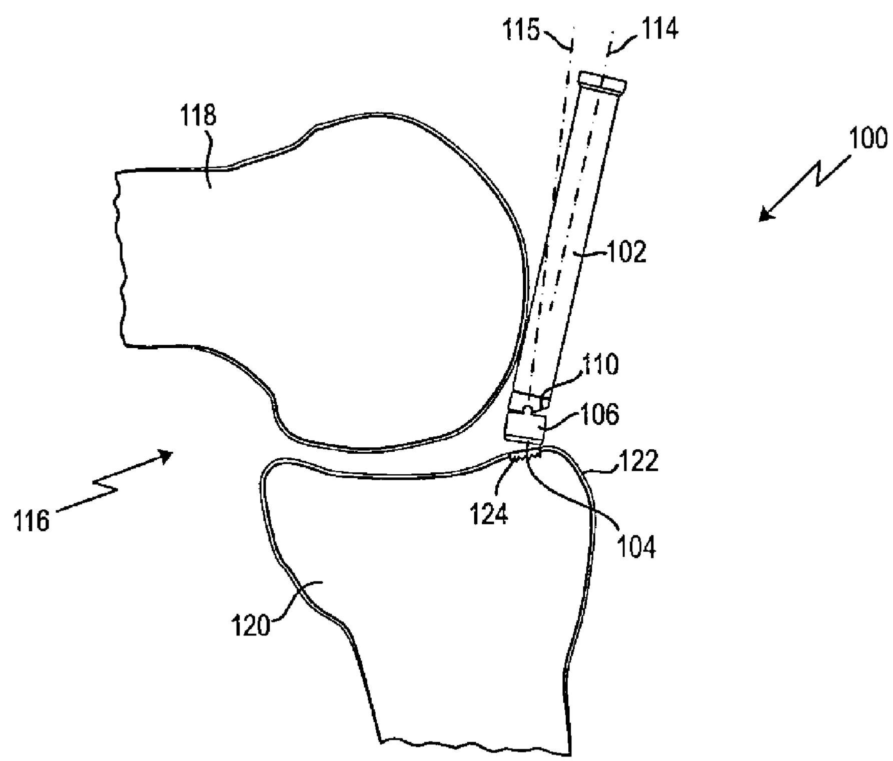
FIG. 9 shows a highly schematic representation of a use example on the basis of a fourth illustrative embodiment, which is similar to the illustrative embodiment of FIG. 1, in the form of a cartilage punch applied to a bone surface of the lower leg in the area of the knee joint.
Figure 10:
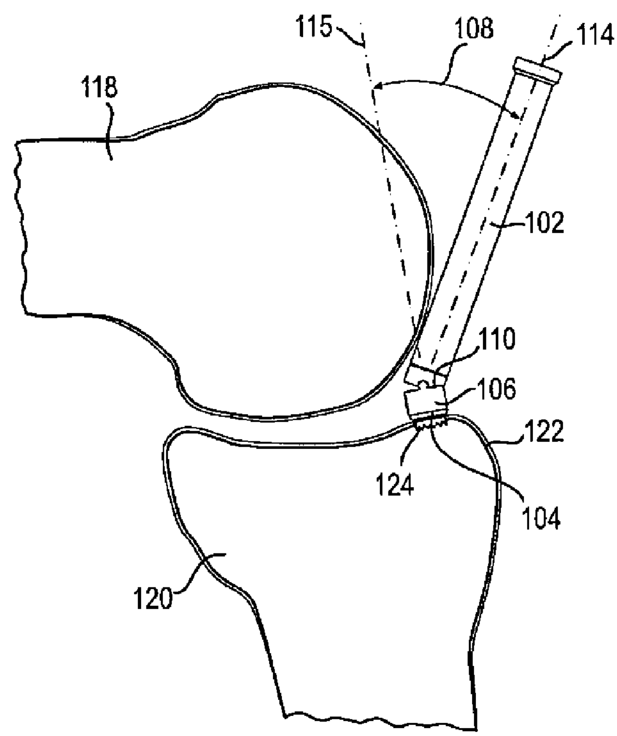

FIGS. 9 and 10 show a practical application of such puncturing devices, in this case with a fourth illustrative embodiment of a puncturing device 100 being shown which is in principle of the same design as the puncturing device 10 in FIGS. 1 to 3, with the only difference that here the maximum pivoting angle 108 is approximately 30°.

Accordingly, the puncturing device 100 has a hollow cylindrical shaft 102, which is connected via a hinge joint to a hollow cylindrical tool carrier 106, of which the tool is designed as a punch 104. Here too, a stop 110 limits the maximum pivoting angle 108 of 30° in one direction from the longitudinal axis 114 of the shaft 102.

FIG. 9 shows a knee joint 116, of which only the femur 118 and the tibia 120 are indicated schematically.

A defect site 124 on the periosteum 122 of the tibia 120 is to be repaired. This defect site 124 has arisen due to the fact that, because of friction with an opposite location on the femur 118 in a normal orientation, that is to say in a standing position, a defect has arisen on the periosteum.

With a rectilinearly oriented, rigid bone punch of the kind mentioned in the introduction, the defect site 124 would not be able to be reached with optimal orientation of the cutter.

FIG. 9 shows how the defect site 124 can already be approached by a slightly oblique shaft 102, which is also already slightly at an angle to the longitudinal axis 115 of the tool 106. The oblique arrangement means that the cutter of the tool 106 meets the approximately plane defect site 124 only in the area of a peripheral point. However, this gives the operator a starting point.

By angling the shaft 102 with respect to the tool carrier 106, the cutter can now be brought to the defect site 124 such that it is located in the correct orientation, that is to say the circumferential cutting edge rests completely on the surface of the periosteum 122 in the area of the defect site 124, as can be seen from FIG. 10. The necessary force can now be applied to the shaft 102 in order to press the punch 104 into the bone 120 and thereby punch out a disc-shaped piece of the periosteum 122 around the defect site 124. A sufficient pressing-in force can be applied even in the maximum angle position of 30° with respect to the longitudinal axis 114 as shown in FIG. 10. It is expedient to adopt the maximum pivoting angle 108, since then the tool carrier 106 and the distal end of the shaft 102 are in contact via the stop 110 and the pressing-in force can be fed through these. A spatula can now be guided through the hollow cylindrical bodies of shaft 102 and tool carrier 106 in order to remove the punched-out piece of periosteum. The puncturing device 100 is then withdrawn.

If it is desired to introduce a microfracture at the defect site, in order to allow suitable fluid to emerge from the bone 120 and form a new periosteum at this location, or in order to permit better fusion of an implant that is to be fitted, a puncturing device 40 or 70 shown in FIGS. 4 to 6 and FIGS. 7 to 8, respectively, can be used, in which case the size or diameter of the respective tool carrier 46, 106 is dimensioned such that it corresponds to the diameter of the punched-out area in the bone 120. By striking the handle 49 or 96 or by pressing in firmly with a hand gripping this handle, it is then possible to drive the corresponding multi-microfracture chisel 48 or 78 into the bone.

Depending on the space between the bones 118 and 120, the overall length of the tool carrier is between 10 and 30 mm.

The more the defect site 124 is inside the knee joint 116 the more is the maximum angle the tool carrier can pivot.

In both cases, by virtue of the fact that the actual tool can be pivoted or angled, these tools can also be used to treat locations that are difficult to access.

What is claimed is:

1. A medical puncturing device for penetrating into a bone or a cartilage, comprising:

a shaft having a longitudinal axis, said shaft having a distal end and a proximal end, a handle provided at said proximal end of said shaft for gripping and moving said shaft along its longitudinal axis during a puncture action, a tool carrier having a distal end and a proximal end, said tool carrier having a longitudinal axis, a puncturing tool arranged at said distal end of said tool carrier, said puncturing tool being a punch or a multi-fracture chisel, said tool carrier being connected at its proximal end via a freely articulated joint to said distal end of said shaft, a central web projecting distally from said distal end of said shaft, said central web extending between two proximally protruding fork arms projecting from said proximal end of said tool carrier, an axle extending through said central web and said two fork arms for connecting said shaft and said tool carrier in an articulating manner, said tool carrier can pivot about said axle from an orientation having said axis of said shaft and said axis of said tool carrier coaxial and an orientation having said axis of said tool carrier pivoted laterally, with said axis of said tool carrier standing under an angle to said axis of said shaft, and a stop limiting said laterally pivoting movement of said tool carrier to a maximum angle of 45°, for minimizing a risk of tilting said tool carrier from a bone surface when acting forces along said longitudinal axis of said shaft via said handle.

2. The medical puncturing device of claim 1, wherein said stop limits said laterally pivoting movement of said tool carrier to a maximum angle of 30°.

3. The medical puncturing device of claim 1, wherein said stop limits said laterally pivoting movement of said tool carrier to a maximum angle of 15°.

4. The medical puncturing device of claim 1, wherein said tool carrier has an axial length of at most 30 mm.

5. The medical puncturing device of claim 1, wherein said tool carrier has an axial length of at most 20 mm.

6. The medical puncturing device of claim 1, wherein said tool carrier has an axial length of at most 10 mm.

7. The medical puncturing device of claim 1, wherein said joint has said axle extending transversely with respect to said longitudinal axis of said shaft, and wherein said tool carrier being freely pivotable about said axle.

8. The medical puncturing device of claim 1, wherein said stop is an oblique stop surface provided on said distal end of said shaft.

9. The medical puncturing device of claim 1, wherein said stop is a stop surface provided at said proximal end of said tool carrier, said stop surface abuts at said distal end of said shaft when said maximum angle is achieved.

* * * * *